(12) United States Patent
Rice et al.

(10) Patent No.: US 11,471,573 B2
(45) Date of Patent: Oct. 18, 2022

(54) WOUND THERAPY SYSTEM WITH WOUND VOLUME ESTIMATION

(71) Applicant: KCI LICENSING, INC., San Antonio, TX (US)

(72) Inventors: Justin Rice, San Antonio, TX (US); Shannon C. Ingram, Bulverde, TX (US); Brett L. Moore, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 378 days.

(21) Appl. No.: 16/366,308

(22) Filed: Mar. 27, 2019

(65) Prior Publication Data

US 2020/0306426 A1 Oct. 1, 2020

(51) Int. Cl.
*A61M 1/00* (2006.01)
*A61F 13/00* (2006.01)

(52) U.S. Cl.
CPC ..... *A61M 1/0062* (2013.01); *A61F 13/00068* (2013.01); *A61M 1/0003* (2013.01); (Continued)

(58) Field of Classification Search
CPC ........ A61M 1/0062; A61M 1/74; A61M 1/90; A61M 1/0003; A61M 2205/15;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion on International Patent Application No. PCT/US2019/024299 dated Feb. 12, 2020 (17 pages).

(Continued)

*Primary Examiner* — Andrew J Mensh

(57) ABSTRACT

A volume of a wound is estimated using a dynamic pressure response measured during instillation of fluid to the wound using a negative pressure wound therapy system. A previously estimated wound volume may be used to detect and prevent overfill of fluid to the wound during future instillation events. For example, real-time pressure measurements may be compared to model data representative of expected pressure at a wound having a volume equal to the previously estimated wound volume, with instillation being stopped if the observed pressure varies from the expected pressure. A comparison of a total volume of fluid instilled to the wound may also be compared to the previously estimated wound volume to prevent overfill. The comparison of wound volume estimated based on an instillation event may also be compared to a wound volume estimated using other methods to provide a higher confidence wound volume estimate.

11 Claims, 5 Drawing Sheets

(52) U.S. Cl.
CPC ............... *A61M 1/74* (2021.05); *A61M 1/90* (2021.05); *A61M 2205/15* (2013.01); *A61M 2205/18* (2013.01); *A61M 2205/3344* (2013.01); *A61M 2205/3379* (2013.01); *A61M 2205/50* (2013.01)

(58) Field of Classification Search
CPC .. A61M 2205/3344; A61M 2205/3379; A61M 2205/18; A61M 2205/50; A61M 1/964; A61M 1/85; A61M 2205/52; A61M 3/0216; A61M 3/0208; A61M 3/0258; A61M 3/022; A61F 13/00068; A61B 5/1076; A61B 5/445
USPC ......................................................... 604/319
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2013/0211318 A1* | 8/2013 | Croizat | A61M 1/85 604/23 |
| 2013/0211348 A1* | 8/2013 | Randolph | A61F 13/00068 604/290 |
| 2015/0032031 A1* | 1/2015 | Hartwell | A61B 5/742 600/587 |
| 2015/0165182 A1* | 6/2015 | Pratt | A61M 39/22 604/290 |
| 2016/0361475 A1* | 12/2016 | Heaton | A61F 13/00068 |
| 2018/0042521 A1* | 2/2018 | Ryu | A61B 5/1073 |
| 2019/0365961 A1* | 12/2019 | Walti | A61M 1/777 |

FOREIGN PATENT DOCUMENTS

| | | | |
|---|---|---|---|
| AU | 755496 B2 | 12/2002 | |
| CA | 2005436 A1 | 6/1990 | |
| DE | 26 40 413 A1 | 3/1978 | |
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| EP | 17150814 * | 1/2017 | ............ A61M 1/777 |
| GB | 692578 A | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |

(56) References Cited

FOREIGN PATENT DOCUMENTS

| JP | 4129536 B2 | 8/2008 |
|---|---|---|
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | WO-2019/023311 A1 | 1/2019 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al.; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al.; "Vacuum Treatment in the Surgical Management of Purulent Wounds"; Vestnik Khirurgi, Sep. 1986, pp. 18-21 and 6 page English translation thereof.
Davydov, Yu. A., et al.; "Vacuum Therapy in the Treatment of Purulent Lactation Mastitis"; Vestnik Khirurgi, May 14, 1986, pp. 66-70, and 9 page English translation thereof.
Yusupov. Yu.N., et al.; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, The Use of Hypermia in the Postoperative Treatment of Lesions of the Extremities and Thorax, Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

\* cited by examiner

WOUND THERAPY SYSTEM WITH WOUND VOLUME ESTIMATION

BACKGROUND

The present disclosure relates generally to a wound therapy system, and more particularly to a wound therapy system configured to estimate a volume relative to a wound site.

Negative pressure wound therapy (NPWT) is a type of wound therapy that involves applying a negative pressure to a wound site to promote wound healing. Recent advancements in wound healing with NPWT involve applying topical fluids to wounds to work in combination with NPWT. However, it can be difficult to determine the appropriate volume of instillation fluid to deliver to the wound. Additionally, it can be difficult to accurately monitor and track healing progression of the wound over time. Accordingly, it would be advantageous to provide a system and method that would allow for accurate and reliable estimation of available space at a wound site into which instillation fluid could be delivered and estimation of the healing progression of the wound site over time. Advantageously, such a system and method would additionally allow for such volume determinations to be performed automatically by a controller, could be performed at any stage during the NPWT treatment, would not require any additional time and/or steps to perform than would a typical NPWT treatment, would allow for overfill detection and/or prevention during fluid instillation cycles, and/or could account for changes in the type or size of removed fluid canister used over the course of the NPWT treatment.

SUMMARY

In one implementation of the present disclosure, a method includes operably connecting a first end of a fluid tube to a fluid canister and a pump of a therapy device and a second end of the fluid tube to a wound dressing applied to a wound site. The pump is operated until a predetermined first negative pressure is detected. A first quantity of fluid is instilled to the wound site until a first predetermined target pressure is detected. Pressure is monitored during installation of the first quantity of fluid to the wound site. A volume of the first quantity of fluid instilled to the wound site is determined using pressure measurements obtained from the monitored pressure e during the installation of the first quantity of fluid to the wound site.

According to some embodiments, the determination of the volume of the first quantity of fluid instilled to the wound site includes comparing the obtained pressure measurements to model pressure decay data. According to some embodiments, the model pressure decay data is representative of pressure decay within a container having a known volume as a predetermined quantity of fluid is instilled to the container. According to some embodiments, the model pressure decay data comprises pressure decay data for a plurality of containers having known volumes.

According to some embodiments, the determined volume of the first quantity of fluid instilled to the wound site is stored. According to some embodiments, the first predetermined target pressure is approximately 0 mmHg. According to some embodiments, the pump is operated until a predetermined second negative pressure is detected. According to some embodiments, a second quantity of fluid is instilled to the wound site until a second predetermined target pressure is detected. According to some embodiments, pressure is monitored during instillation of the second quantity of fluid to wound site.

According to some embodiments, a volume of the second quantity of fluid instilled to the wound site is determined using pressure measurements obtained from the monitored pressure during the installation of the second quantity of fluid to the wound site. According to some embodiments, the second predetermined target pressure is approximately 0 mmHg.

According to some embodiments, the first quantity of fluid is instilled to the wound site at a predetermined flow rate. According to some embodiments, the second quantity of fluid is instilled to the wound site at a predetermined flow rate. According to some embodiments, the determined volume of the second quantity of fluid instilled to the wound site is stored. According to some embodiments, a rate of wound healing is determined by comparing the first stored volume to the second stored volume.

In one implementation of the present disclosure, a method of preventing overfill of fluid to a wound site includes operably connecting a first end of a fluid tube to a fluid canister and a pump of a therapy device and a second end of the fluid tube to a wound dressing applied to a wound site. The pump is operated to attain a predetermined first negative pressure. Fluid is instilled to the wound site. Pressure during instillation of the fluid to the wound site is monitored. Instillation of fluid to the wound site is stopped in response to a first predetermined target pressure being detected.

According to some embodiments, the first predetermined target pressure is 0 mmHg. According to some embodiments, a volume of the wound site is estimated prior to the instillation of fluid to the wound site. According to some embodiments, model pressure decay data representative of pressure decay within a container having a volume equal to the estimated volume of the wound site as varying quantities of fluid are instilled into the container is obtained. According to some embodiments, monitoring pressure includes obtaining measurements of the pressure. According to some embodiments, the obtained pressure measurements are compared to the model pressure decay data in real-time. According to some embodiments, an alarm is generated if the measured pressure does not correspond to the model pressure decay data.

According to some embodiments, a volume of the fluid instilled to the wound site is determined. According to some embodiments, the volume of the fluid instilled to the wound site is determined using pressure measurements obtained from the monitored pressure during instillation of the fluid to the wound site. According to some embodiments, determining the volume of the fluid instilled to the wound site includes comparing the obtained pressure measurements to model pressure decay data.

According to some embodiments, the second predetermined pressure is 0 mmHg. According to some embodiments, the estimated volume of the wound site is compared to the determined volume of the fluid instilled to the wound site. According to some embodiments, an alarm is generated if the estimated volume of the wound site is not substantially the same as the determined volume of the fluid instilled to the wound site.

In one implementation of the present disclosure, a wound therapy system includes a pump, a wound dressing configured to be applied to a wound site, a fluid tube fluidly connecting the pump to the wound dressing, and a controller. The controller is configured to monitor pressure during instillation of a fluid to the wound site and determine a volume of the fluid instilled to the wound site using pressure measurements obtained from the monitored pressure during the instillation of the fluid to the wound site.

According to some embodiments, the controller is configured to determine the volume of the fluid instilled to the wound by comparing the obtained pressure measurements to model pressure decay data. According to some embodiments, the controller is configured to store the determined volume of the fluid instilled to the wound site. According to some embodiments, the controller is configured to determine a volume of a fluid instilled to the wound site at each of one or more instillation events occurring during treatment of the wound site. According to some embodiments, the controller is configured to store each of the determined volumes. According to some embodiments, the controller is configured to monitor healing of the wound site based on the stored determined volumes.

According to some embodiments, the wound therapy system also includes a source of instillation fluid. The controller is further configured to operate the pump to instill the fluid to the wound site. According to some embodiments, the controller is configured to stop the instillation of the fluid to the wound site when a first predetermined pressure has been. According to some embodiments, the controller is configured to stop the operation of the pump when a pressure of substantially 0 mmHg has been detected. According to some embodiments, the controller is further configured to operate the pump to evacuate air from the wound site.

According to some embodiments, the controller is further configured to operate the pump to evacuate air from the wound site to attain a predetermined negative pressure. Upon detecting that a pressure is equal to the predetermined negative pressure, the controller is configured to operate the pump to instill a fluid to the wound site. The controller is configured to stop the instillation of fluid to the wound site upon detection that a measured pressure is equal to a predetermined target pressure.

In one implementation of the present disclosure, a wound therapy system includes a pump, a wound dressing configured to be applied to a wound site, a fluid tube fluidly connecting the pump to the wound dressing, a source of instillation fluid, and a controller. The controller is configured to operate to pump to instill the instillation fluid to the wound site and monitor pressure during instillation of fluid to the wound site. The controller is configured to stop the operation of the pump in response to the detection of a first predetermined pressure.

According to some embodiments, the predetermined pressure is 0 mmHg. According to some embodiments, the controller is configured to obtain an estimated volume of the wound site prior to operating the pump to instill fluid to the wound site. According to some embodiments, the controller is configured to obtain pressure measurements based on the pressure monitored during the operation of the pump to instill fluid to the wound site. According to some embodiments, the controller is configured to obtain model pressure decay data representative of pressure decay within a container having a volume equal to the estimated volume of the wound site as fluid is instilled into the container. According to some embodiments, the controller is further configured to compare the pressure measurements to the model pressure decay data in real-time.

According to some embodiments, an alarm is generated if the measured pressure does not correspond to the model pressure decay data. According to some embodiments, the estimated volume of the wound site is obtained by the controller by operating the pump to evacuate air from the wound site.

According to some embodiments, the controller is further configured to operate the pump to evacuate air from the wound site and monitor pressure as air is evacuated from the wound site. The controller is further configured to stop operation of the pump when a predetermined negative pressure has been detected. According to some embodiments, the controller is configured to operate the pump to instill the instillation fluid to the wound site after the predetermined negative pressure has been detected.

According to some embodiments, the controller is configured to estimate the volume of the fluid instilled to the wound site using pressure measurements obtained from the monitored pressure during instillation of the fluid to the wound site. According to some embodiments, the controller is configured to compare the obtained pressure measurements to model pressure decay data to estimate the volume of the fluid instilled to the wound site According to some embodiments, the model pressure decay data is representative of pressure decay within a container having a known volume during instillation of a fluid into the container.

According to some embodiments the controller is configured to obtain an estimate of the volume of the wound site. According to some embodiments the estimated volume of the wound site is compared to the determined volume of the fluid instilled to the wound site. According to some embodiments an alarm is generated if the estimated volume of the wound site is not substantially the same as the determined volume of the fluid instilled to the wound site.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Overview

Figure 1:
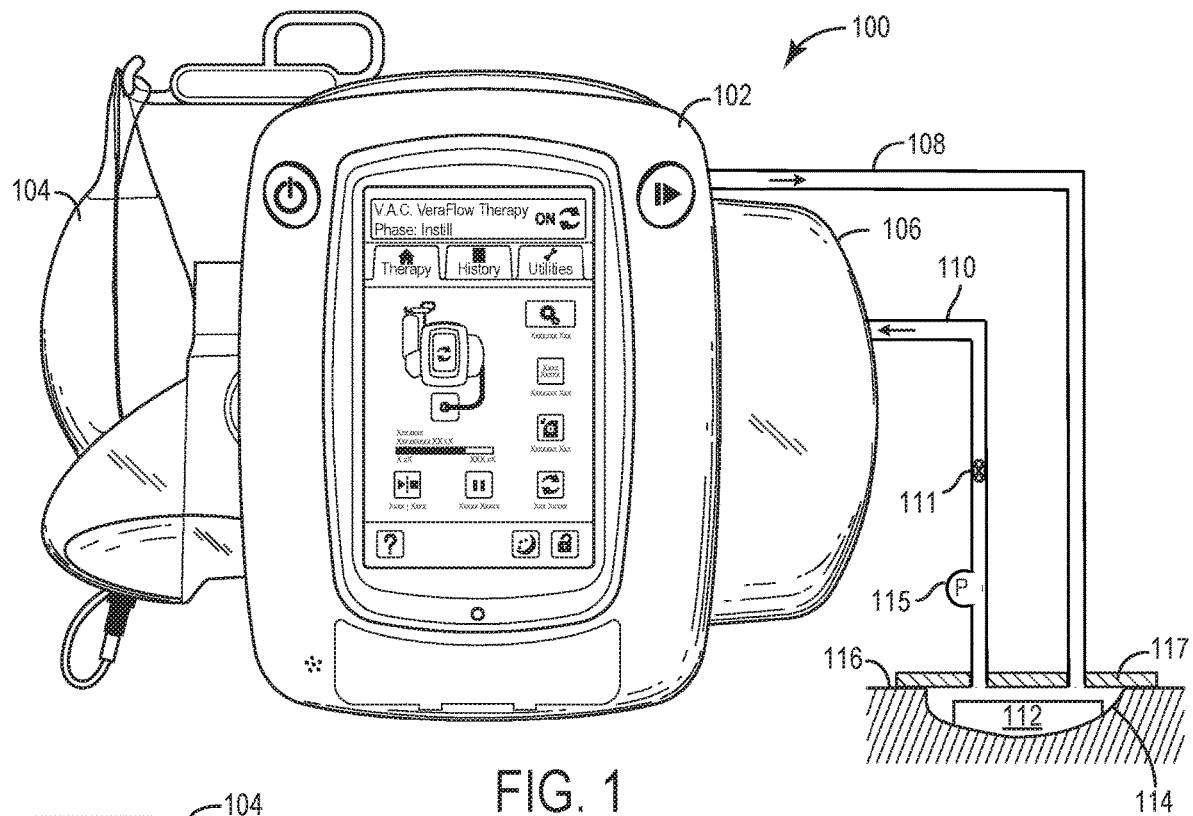
FIG. 1 is a block diagram of a negative pressure wound therapy system including a therapy device coupled to a wound dressing via tubing, according to an exemplary embodiment.

Referring generally to the FIGURES, a wound therapy system is shown according to various exemplary embodiments. The wound therapy system may include a therapy device and a wound dressing. The therapy device may include an installation fluid canister, a removable fluid canister, a valve, a pneumatic pump, an installation pump, and a controller. The wound dressing can be applied to a patient's skin surrounding a wound. The therapy device can be configured to deliver installation fluid to the wound and provide negative pressure wound therapy (NPWT) by maintaining the wound at negative pressure. Components of the wound therapy device, the wound dressing, and the wound site form a negative pressure circuit.

The controller may be configured to operate the pneumatic pump, the installation pump, and/or other controllable components of the therapy device. According to some embodiments in which the NPWT treatment provided using the NPWT system includes the installation of installation fluid to the wound site, the controller may be configured to estimate the volume of the wound site and/or a volume of a quantity of installation fluid delivered to the wound site based on a comparison of dynamic pressure responses observed as fluid is instilled to the wound site to model pressure response data. Because the dynamic pressure responses are observed simultaneously with the installation of fluid to the wound site, the system and methods described herein are configured to allow the controller to estimate wound site volume without requiring any additional steps and/or time than would otherwise be required to provide installation therapy treatment using the NPWT system.

According to some embodiments, the wound site volume estimate based on dynamic pressure responses observed during fluid installation may be used to verify and/or may be verified using wound site volume estimates obtained using any other number of methods to provide the NPWT system with higher confidence wound site volume estimates. For example, in some embodiments, the controller may compare the wound site volume estimated based on dynamic pressure responses observed during fluid installation to a wound site volume estimated based on a comparison of dynamic pressure responses observed during the purging of negative pressure within the entirety and/or selected portions of the negative pressure circuit.

In various embodiments, the controller may additionally, or alternatively, be configured to prevent and/or detect overfill during the installation of installation fluid to the wound site. According to some such embodiments, the controller may use a previously obtained wound site volume estimate (estimated, e.g., during a prior installation of fluid to the wound site; based on a comparison of dynamic pressure responses observed during the purging of negative pressure from the negative pressure circuit; etc.) as a backstop value against which the volume of the quantity of fluid that has been instilled to the wound site is compared to prevent overfilling the wound site with installation fluid. In some embodiments, the previously obtained wound site volume estimate may additionally, or alternatively, be used to identify a model pressure decay curve representative of a dynamic pressure response that would be expected during the installation of installation fluid to the wound site to attain a predetermined target pressure, as measured, e.g., at any one or more of the wound site, within the tubing fluid connected the wound site to the therapy device, within the removed fluid canister, at the therapy device, etc. In such embodiments, dynamic pressure response at the wound site is monitored in real-time and compared against the model pressure decay curve, with deviations in the monitored pressure at and the expected pressure based on the model decay curve being used to alert the controller to a possible overfill situation which may need to be addressed.

In some embodiments, the controller may additionally, or alternatively, estimate and monitor the volume of the wound site at a plurality of times during wound treatment, with the controller determining healing progression of the wound site based on changes in the estimated wound site volume over the course of NPWT treatment. By monitoring the healing progression of the wound site, the controller may be configured to alert a user if the healing of the wound site is not progressing as intended or expected. As will be understood, in some embodiments, the monitoring of changes in estimated wound site volume over time may additionally advantageously provide the controller with more accurate values that allow the controller to more accurately detect and/or prevent overfill of installation fluid to the wound site. These and other features of the wound therapy system are described in detail below.

Wound Therapy System

Referring now to FIG. 1, a negative pressure wound therapy (NPWT) system 100 is shown according to an exemplary embodiment. The NPWT system 100 is shown to include a therapy device 102 fluidly connected to a wound dressing 112 via tubing 108 and 110. According to various embodiments, a wound dressing 112 may be placed on or within the wound site 114 and adhered or sealed to a patient's skin 116 surrounding a wound site 114 using drape layer 117. Several examples of wound dressings 112 which can be used in combination with NPWT system 100 are described in detail in U.S. Pat. No. 7,651,484 granted Jan. 26, 2010, U.S. Pat. No. 8,394,081 granted Mar. 12, 2013, and U.S. patent application Ser. No. 14/087,418 filed Nov. 22, 2013. The entire disclosure of each of these patents and patent applications is incorporated by reference herein.

Figure 2:
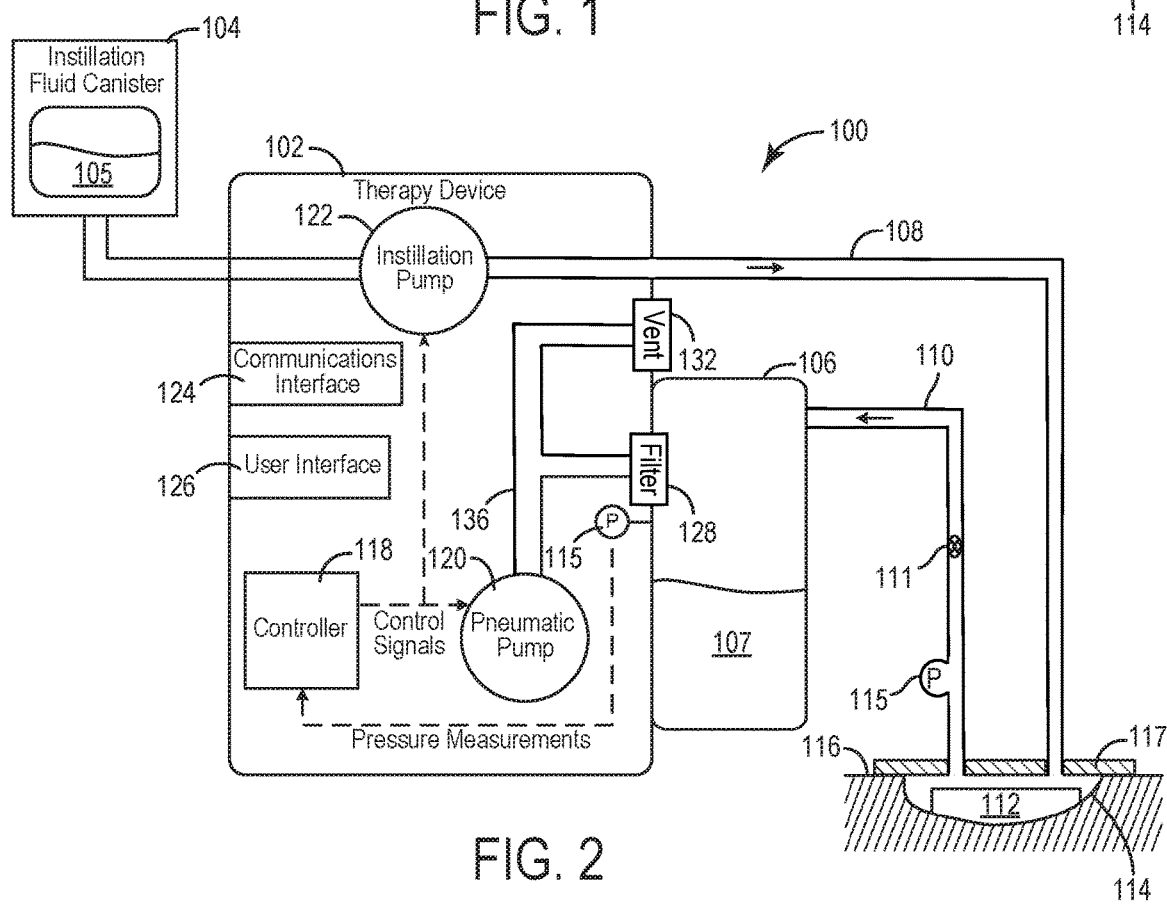
FIG. 2 is a block diagram illustrating the negative pressure wound therapy system of FIG. 1 in greater detail, according to an exemplary embodiment.

As illustrated by the block diagram of FIG. 2, in general the therapy device 102 includes a pneumatic pump 120, an installation pump 122, a filter 128, and a controller 118. Pneumatic pump 120 can be fluidly coupled to removed fluid canister 106 (e.g., via conduit 136) and can be configured to draw a vacuum within canister 106 by pumping air out of canister 106. In some embodiments, pneumatic pump 120 is configured to operate in both a forward direction and a reverse direction. For example, pneumatic pump 120 can operate in the forward direction to pump air out of canister 106 and decrease the pressure within canister 106. Pneumatic pump 120 can operate in the reverse direction to pump air into canister 106 and increase the pressure within canister 106. Pneumatic pump 120 can be controlled by controller 118, described in greater detail below.

Therapy device 102 can be configured to provide negative pressure wound therapy by reducing the pressure at wound site 114. Therapy device 102 can draw a vacuum at wound site 114 (relative to atmospheric pressure) by removing wound exudate, air, and other fluids from wound site 114. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids 121 removed from wound site 114 may include instillation fluid 105 previously delivered to wound site 114. Instillation fluid 105 can include, for example, a cleansing fluid, a prescribed fluid, a medicated fluid, an antibiotic fluid, or any other type of fluid which can be delivered to wound site 114 during wound treatment. Instillation fluid 105 may be held in an instillation fluid canister 104 and controllably dispensed to wound site 114 via tubing 108. In some embodiments, instillation fluid canister 104 is detachable from therapy device 102 to allow canister 104 to be refilled and replaced as needed.

Instillation pump 122 can be fluidly coupled to instillation fluid canister 104 and the wound dressing 112 via instillation tubing 108. Instillation pump 122 can be operated to deliver instillation fluid 105 to wound dressing 112 and wound site 114 by pumping instillation fluid 105 through instillation tubing 108. Instillation pump 122 can be controlled by controller 118, described in greater detail below. According to some embodiments, the instillation pump 122 may be defined by all or a portion of the pneumatic pump 120.

Filter 128 can be positioned between removed fluid canister 106 and pneumatic pump 120 (e.g., along conduit 136) such that the air pumped out of canister 106 passes through filter 128. Filter 128 can be configured to prevent liquid or solid particles from entering conduit 136 and reaching pneumatic pump 120. Filter 128 may include, for example, a bacterial filter that is hydrophobic and/or lipophilic such that aqueous and/or oily liquids will bead on the surface of filter 128. Pneumatic pump 120 can be configured to provide sufficient airflow through filter 128 that the pressure drop across filter 128 is not substantial (e.g., such that the pressure drop will not substantially interfere with the application of negative pressure to wound site 114 from therapy device 102).

Removed fluid canister 106 may be a component of therapy device 102 configured to collect wound exudate and other fluids 121 removed from wound site 114. In some embodiments, removed fluid canister 106 is detachable from therapy device 102 to allow canister 106 to be emptied and replaced as needed. A lower portion of canister 106 may be filled with wound exudate and other fluids 107 removed from wound site 114, whereas an upper portion of canister 106 may be filled with air. Therapy device 102 can be configured to draw a vacuum within canister 106 by pumping air out of canister 106. The reduced pressure within canister 106 can be translated to wound dressing 112 and wound site 114 via tubing 110.

As shown in FIG. 1, disposed along tubing 110 at a location between the removed fluid canister 106 and the wound site 114 may be a tubing valve 111 (e.g. spring-biased; duck-bill; check-valve, etc.) configured to prevent fluid flow from the removed fluid canister 106 to the wound site 114.

Figure 3:
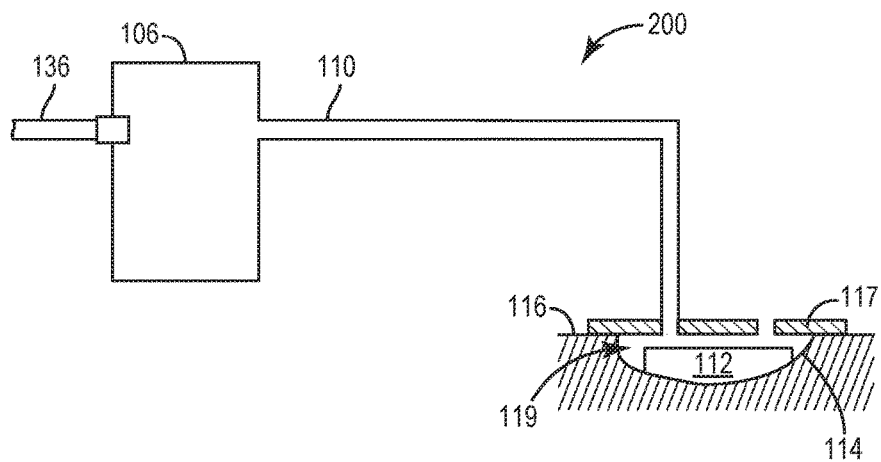
FIG. 3 is a block diagram illustrating the negative pressure circuit, the removed fluid canister circuit and the wound site circuit of the negative pressure wound therapy system of FIG. 1 in greater detail, according to an exemplary embodiment.

Referring to the block diagram of FIG. 3, removed fluid canister 106, tubing 110, conduit 136 extending between pneumatic pump 120 and removed fluid canister 106, and wound site 114 are fluidly connected to define a negative pressure circuit 200. As will be discussed in more detail below, the volumes of the tubing 110 and conduit 136 define known volumes which can be easily subtracted from or otherwise factored into calculations of volume(s) relative to the wound site 114. As shown in FIG. 2, according to various embodiments, a vent 132 may be provided via which a vacuum within the negative pressure circuit 200 may be purged.

As will be described with more reference to FIG. 8, according to some embodiments, it may be desired to verify the volume estimated using any of the methods described herein against a volume estimate obtained using other methods and/or from other sources, such as, e.g. a volume estimated based on measurements obtained during a drawdown of the negative pressure circuit, such as, e.g. described in in related, co-pending U.S. Provisional Application 62/714,229, filed Aug. 3, 2018 and titled WOUND THERAPY SYSTEM WITH WOUND VOLUME ESTIMATION, the entire disclosure of which is incorporated by reference herein. Accordingly, as illustrated by FIG. 4, according to various embodiments, the NEWT system 100 may optionally include one or more features configured to enable to the NEWT system 100 to be used to estimate volume using any number of other methods in addition to the various methods of estimating volume during fluid instillation described herein.

Figure 4:
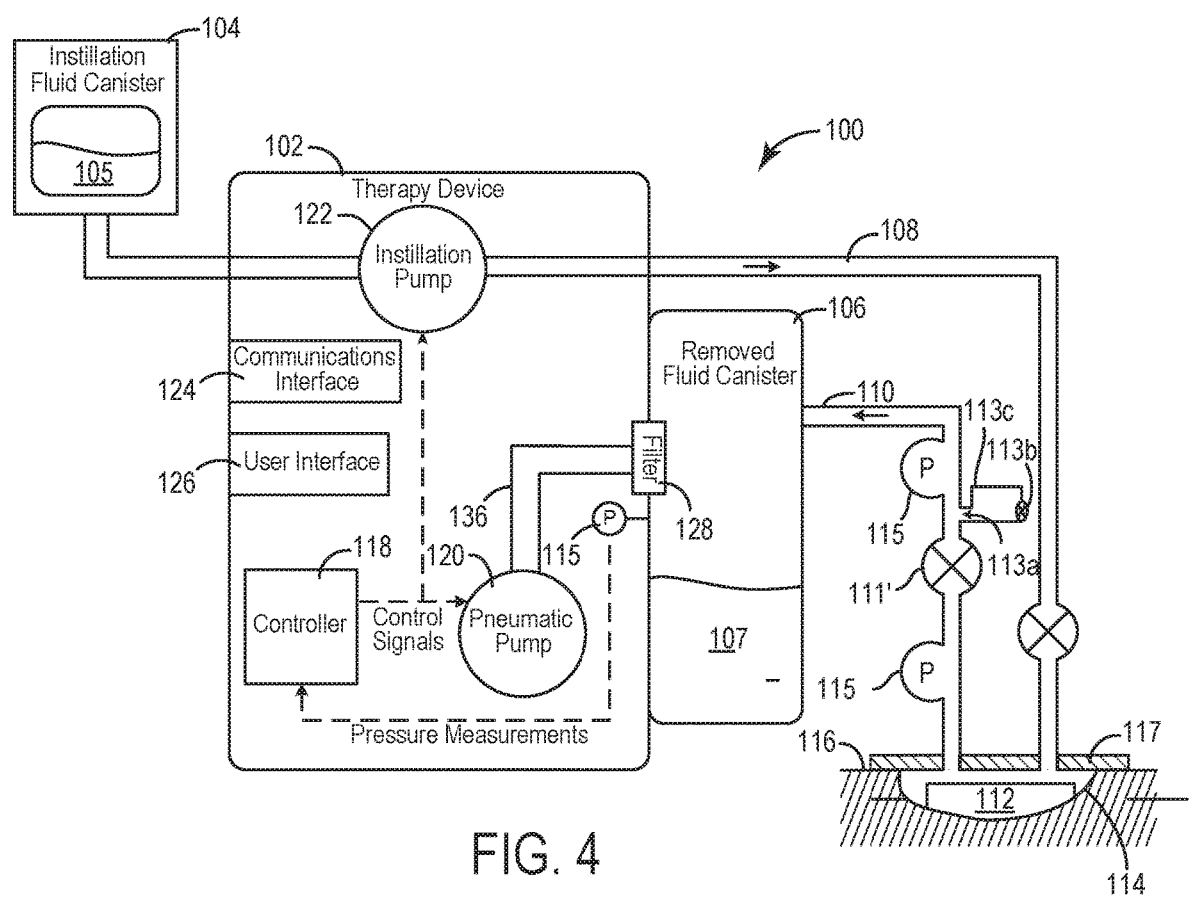
FIG. 4 is a block diagram illustrating a negative pressure wound therapy system, according to an exemplary embodiment.

For example, as illustrated in FIG. 4, the NEWT system 100 may include features similar to those described with reference to the various systems described in related, co-pending U.S. Provisional Application 62/714,229. In particular, according to some embodiments, the tubing valve 111 described with reference to the embodiment of FIG. 1 may be modified, with the tubing valve 111' of the embodiment of FIG. 4 being configured to selectively permit and prevent fluid flow between the removed fluid canister 106 and the wound site 114, thus allowing the negative pressure circuit 200 to be selectively fluidly divided into a removed fluid canister circuit (i.e. the portion of the negative pressure circuit located upstream of tubing valve 111') and a wound site circuit (i.e. the portion of negative pressure circuit located downstream of tubing valve 111'). Referring again to FIG. 4, according to some embodiments, the NPWT system 100 may also be provided with a calibrated leak system 113 configured to selectively control and measure airflow between tubing 110 and the ambient environment surrounding therapy device 102. According to various embodiments, calibrated leak system 113 can be selectively opened to allow airflow into tubing 110 at a known, predetermined rate.

As illustrated by the block diagram of FIG. 2, according to various embodiments, the controller 118 may be configured to operate various components of therapy device 102. In particular, as will be described in more detail below, according to various embodiments, the controller 118 may be configured to control the various components of the NPWT system 100 to execute one or more volume determination procedures via which, e.g. an estimated volume of the wound site 114 may be determined, the healing progression of the wound site may be tracked, etc. According to various embodiments, the controller 118 may be configured such that these procedures may be performed with minimal user intervention and/or input.

According to various embodiments, NPWT system 100 may include a variety of sensors. For example, in some embodiments, one or more pressure sensors 115 may be located at any one or more of: in-line in the tubing 110, at the wound dressing 112, at the removed fluid canister 106, at the therapy device 102, at the pump 120, etc., so as to allow for the measurement of pressure at any one or more of the removed fluid canister 106, within the tubing 110 and/or at the wound site 114. Pressure measurements recorded by pressure sensor(s) 115 can be communicated to controller 118. According to various embodiments, controller 118 may use the pressure measurements from pressure sensor(s) 115 as inputs to various pressure testing operations and control operations performed by controller 118.

In some embodiments, therapy device 102 includes a user interface 126. User interface 126 may include one or more buttons, dials, sliders, keys, or other input devices configured to receive input from a user. User interface 126 may also include one or more display devices (e.g., LEDs, LCD displays, etc.), speakers, tactile feedback devices, or other output devices configured to provide information to a user. User interface 126 can also display alerts generated by controller 118. For example, controller 118 can generate a "no canister" alert if canister 106 is not detected.

In some embodiments, therapy device 102 includes a data communications interface 124 (e.g., a USB port, a wireless transceiver, etc.) configured to receive and transmit data. Communications interface 124 may include wired or wireless communications interfaces (e.g., jacks, antennas, transmitters, receivers, transceivers, wire terminals, etc.) for conducting data communications external systems or devices. In various embodiments, the communications may be direct (e.g., local wired or wireless communications) or via a communications network (e.g., a WAN, the Internet, a cellular network, etc.). For example, communications interface 124 can include a USB port or an Ethernet card and port for sending and receiving data via an Ethernet-based communications link or network. In another example, communications interface 124 can include a Wi-Fi transceiver for communicating via a wireless communications network or cellular or mobile phone communications transceivers.

Methods of Use

Figure 5:
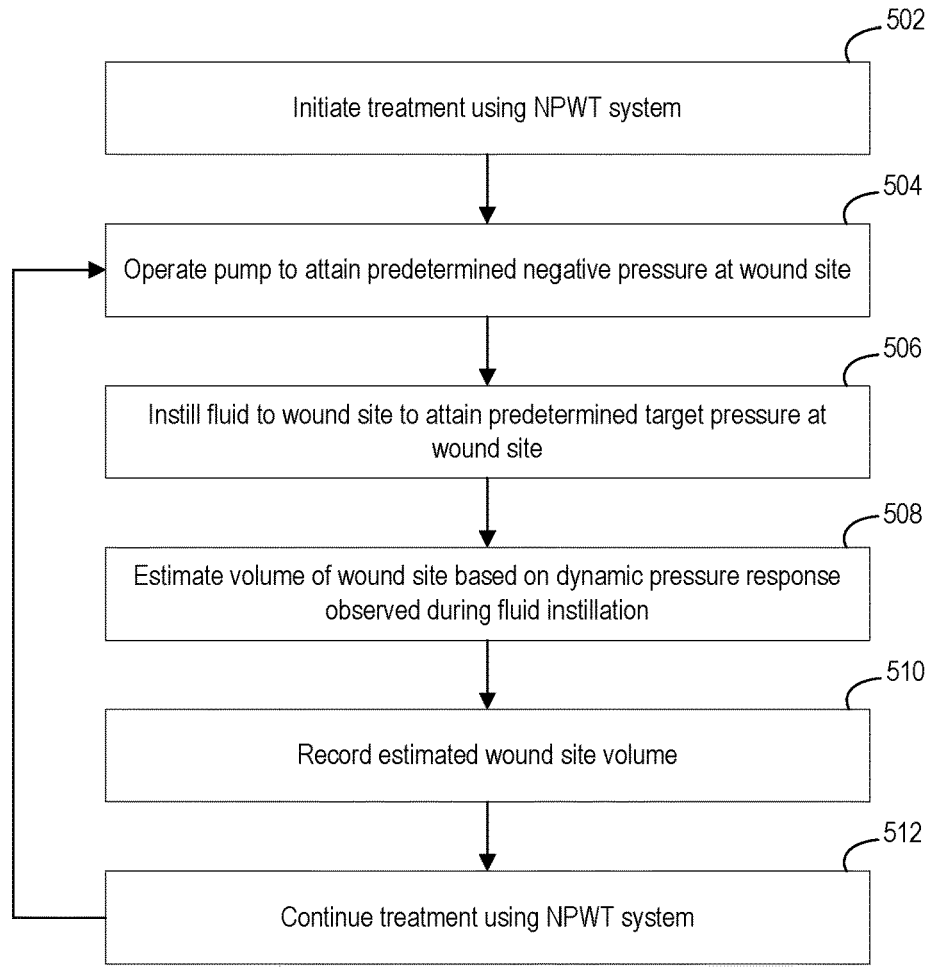
FIG. 5 is a flowchart of a method of using a negative pressure wound therapy system, according to an exemplary embodiment.

Referring to FIG. 5 a flowchart detailing the steps of a method 500 of using a NPWT system 100 is shown according to an exemplary embodiment. As shown in FIG. 5, at step 502, a NPWT system 100 (such as, e.g., illustrated in FIG. 1) is provided, with the drape layer 117 and wound dressing 112 of the NPWT system 100 being positioned at the desired wound site 114 to be treated. According to some embodiments, as a part of the initiation of treatment at step 502, and prior to proceeding with the remaining steps of method 500, any number of different methods may be used to confirm that the drape layer 117 and wound dressing 112 have been appropriately sealed about the wound site 114. For example, according to some embodiments, following the operation of the pneumatic pump 120 to evacuate of air from the wound site 114, pressure may be monitored (e.g. using pressure sensor 115) to confirm the absence of an unintentional leak of air from the wound site 114. According to various embodiments, the pressure that may be monitored may be any one or more of the pressure within tubing 110, within the removed fluid canister 106, at the therapy device 102, at the wound site 114, at the pump 120, etc. As will be understood, in other embodiments, this confirmation of an appropriate seal between the wound dressing 112/drape layer 117 and the wound site 114 may alternatively be performed as a part of and/or during the subsequent steps of the method 500.

In addition to confirming the absence of leaks in the assembled NPWT system 100, according to some embodiments, step 502 may optionally also include the step of obtaining model data. The model data is representative of changes in pressure over time as instillation fluid is instilled to wound sites of varying volumes under a variety of clinically relevant conditions and states (e.g. different instillation rates, wound volumes, dressing/foam characteristics, dressing air leak rates, starting pressures, predetermined target pressure, etc.). Such model data may be generated using any number of, or combination of various function approximators, statistical method, machine learning systems, etc. The model data obtained at step 502 may include any number of different pressure decay curves, functions, lookup tables, etc., and may be obtained as pre-existing information that is input and stored by the controller, and/or may be obtained and processed by the controller 118 during an optional, initial training procedure conducted by the controller 118 prior to the use of the NPWT system 100 to treat wound site 114 (e.g. prior to the initiation of method 500 or as part of the initial setup of the NPWT system 100 at step 502). Non-limiting examples of embodiments of training procedures by which such relationships may be generated by the controller 118 are outlined in related, co-pending U.S. Provisional Application 62/650,132, filed Apr. 17, 2018 and titled WOUND THERAPY SYSTEM WITH WOUND VOLUME ESTIMATION, the entire disclosure of which is incorporated by reference herein. As will be understood, in embodiments in which wound site 114 volume is additionally estimated during the purging of negative pressure within all or portions of the negative pressure circuit 200, model data representative of changes in pressure over time as ambient air is allowed to flow into all or portions of the negative pressure circuit 200 under a variety of clinically relevant conditions and states may additionally be obtained in a substantially similar manner.

Once the set-up of the NPWT system 100 at step 502 is complete, at step 504 the pneumatic pump 120 is operated (either manually or using controller 118) to attain a predetermined negative pressure. After the predetermined target pressure has been attained, the instillation pump 122 (which may be the same as or different from pneumatic pump 120) is operated at step 506 to instill instillation fluid 105 to the wound site 114. Instillation fluid 105 is instilled to the wound site 114 at step 506 until a predetermined target pressure has been attained. According to various embodiments, the target pressure and/or predetermined negative pressure may correspond to a pressure as measured at any one or more of the tubing 110, the removed fluid canister 106, the therapy device 102, at the wound site 114, the pump 120, etc. According to various embodiments, the predetermined target pressure may be between approximately minus 15 mmHg and approximately 15 mmHg, more specifically between approximately minus 5 mmHg and 5 mmHg, and even more specifically approximately 0 mmHg.

At step 508, the pressure decay (such pressure decay may be an increase in pressure over time), monitored at any one or more of the tubing 110, the removed fluid canister 106, the therapy device 102, at the wound site 114, etc. during the instillation of instillation fluid 105 to the wound site 114 at step 506 may be used to estimate the volume of the wound site 114. According to some embodiments, the wound site 114 volume estimation may be based on a comparison of the measured dynamic pressure during the fluid instillation of step 506 to model pressure decay data obtained prior to or during step 502. Because the wound site 114 volume estimated at step 508 is estimated based on pressure decay observed during the instillation of instillation fluid 105 to the wound site 114 at step 506, as noted previously, the method 500 illustrated by the flowchart of FIG. 5 requires no additional steps and/or time than that which would otherwise be required to instill the instillation fluid 105 to the wound site 114. As step 510, the wound site 114 volume estimated at step 508 may optionally be stored for future use.

Following the estimation of wound site 114 volume at step 508, the NPWT system 100 may continue to be used at step 512 to provide NPWT treatment according to any number of different protocols. As illustrated by step 512 of the method 500 of FIG. 5, according to various embodiments, the NPWT treatment may continue with one or more cycles of negative pressure application and fluid instillation using the NPWT system 100 with step 508 of estimating wound site 114 volume optionally being repeated after some, all or none of the additional step 504 of applying negative pressure to the wound site 114 and/or step 506 of instilling instillation fluid 105 to the wound site 114.

Figure 6:
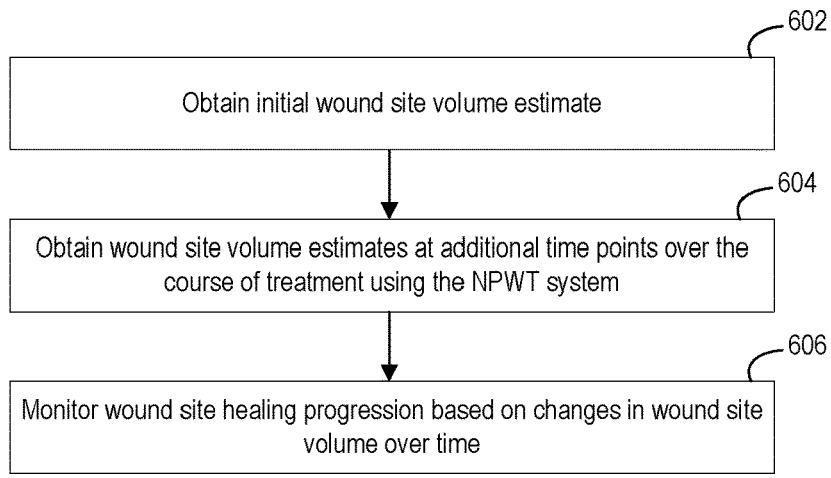
FIG. 6 is a flowchart of a process for monitoring the healing progression of a wound site over time, according to an exemplary embodiment.

The wound site 114 volume estimated using the method 500 of FIG. 5 may be used for any number of different purposes. For example, as noted above, according to some embodiments, the wound site 114 volume estimated during an instillation phase of a NPWT treatment may advantageously be used to track the progress wound site 114 healing. Referring to FIG. 6, a flowchart of a method 600 of monitoring wound site 114 healing by utilizing estimated wound site 114 volume measurements obtained at a plurality of time points during the course of a NPWT treatment using a NPWT system 100 is illustrated according to an exemplary embodiment. As shown FIG. 6, at step 602, an initial wound site 114 volume estimate is recorded at step 602, and may serve as a baseline against which subsequent wound site 114 volume estimates are compared to track healing progress. According to various embodiments, estimation of the initial volume of the wound site 114 at step 602 may be performed according to (or as) step 508 of the method 500 described with reference to FIG. 5.

At step 604, the volume of the wound site 114 is estimated and recorded at one or more additional times during treatment (e.g., once per day) following the estimation of the initial wound site 114 volume at step 602, with the times at which such one or more wound site 114 volumes are estimated and the values of the determined wound site 114 volume being stored as data points within the memory of therapy device 102 and/or presented to a user as an output of therapy device 102 (e.g., via communications interface 124 or user interface 126). In some embodiments, the estimated wound volume can be plotted as a function of time.

The additional wound site 114 volumes estimated at one or more additional times over the course of treatment at step 604 may be estimated according to any number of different methods. For example, according to various embodiments, estimation of the volume of the wound site 114 at step 604 may be performed according to (or as) step 508 of the method 500 of FIG. 5 during subsequent occurrences of fluid instillation as part of the continued NPWT treatment of step 512. Alternatively, or additionally, one or more of the additional wound site 114 volumes estimated at step 604 may be obtained according to any other methods, such as, e.g. based on an observed dynamic pressure response within a negative pressure circuit 200 of the NPWT system 100 during a purging even.

As additional wound site 114 volume estimates are obtained at steps 604, at step 606, changes in the estimated wound site 114 volume over time may be used to determine healing progression of the wound site 114. For example, step 606 may include comparing wound site 114 volume estimates obtained at step 604 to one or more previous estimates of the wound site 114 volume (obtained at either step 604 or step 602) to identify a change in the wound site 114 volume. In some embodiments, step 606 may additionally include determining a rate at which the wound site 114 is healing based on the changes in the estimated wound site 114 volume over time. In some embodiments, step 606 may include extrapolating or predicting a time at which wound site 114 will be fully healed based on the series of wound site 114 volume estimates stored by the controller 118. For example, step 606 may include predicting a time at which the estimated wound site 114 volume will reach zero (or another threshold value) based on the initial wound site 114 volume estimated at step 1002 and the series of additional wound site 114 volumes estimated at step 604.

According to some embodiments, in addition to, or as an alternative to, the use of a wound site 114 volume estimates to monitor wound site 114 healing progression (such as, e.g., described with reference to the method 600 of FIG. 6 above), wound site 114 volume estimates may be used to detect and/or prevent overfill of instillation fluid 105 to the wound site 114 during an instillation of instillation fluid 105 to the wound site 115.

Figure 7:
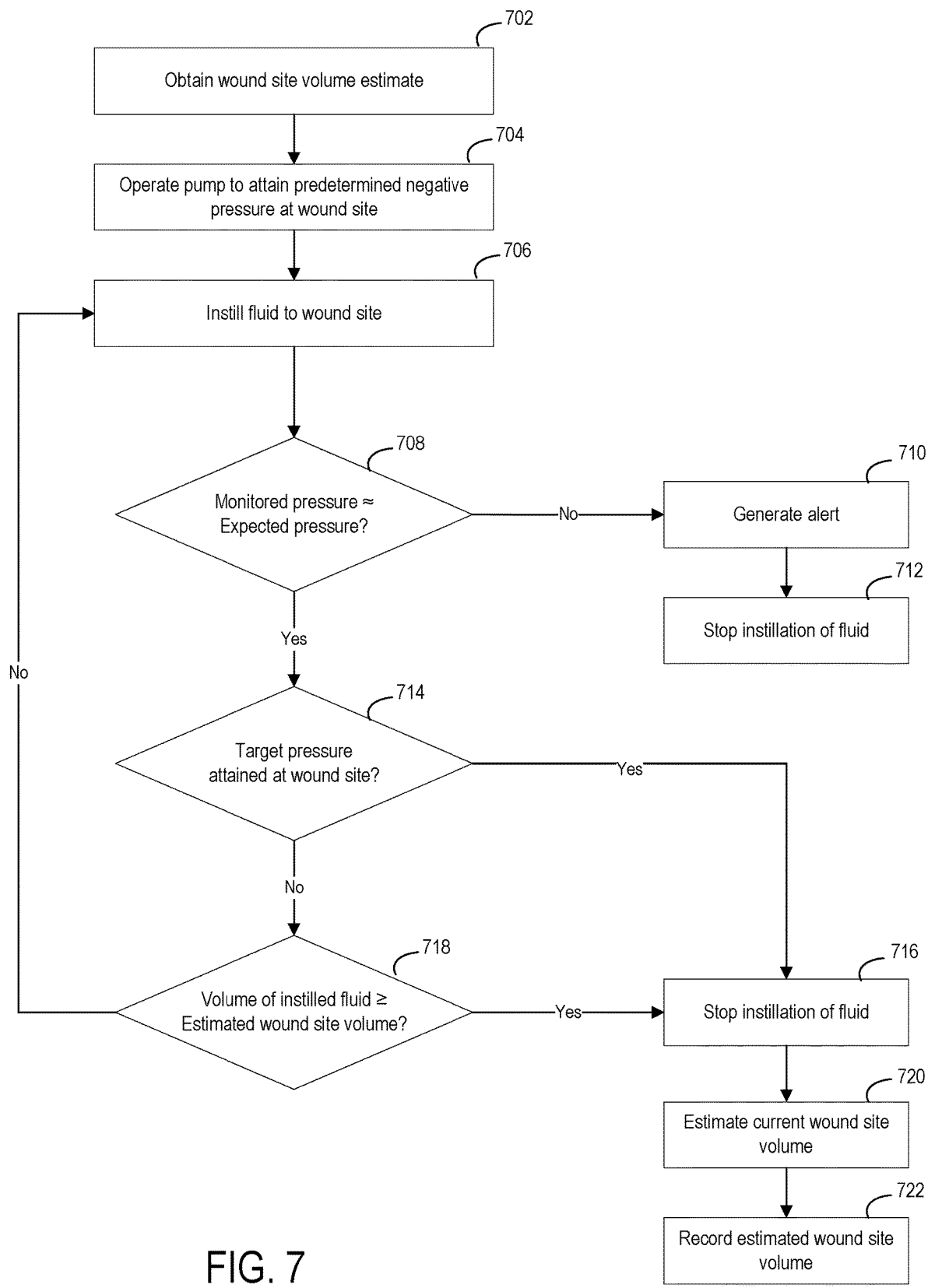
FIG. 7 is a flowchart of a method of using a negative pressure wound therapy system, according to an exemplary embodiment.

Referring to the method 700 of preventing and/or detecting overfill of instillation fluid 105 to a wound site 115 during an instillation event shown in FIG. 7, the method 700 begins at step 702 with obtaining an initial wound site 114 volume estimate. In embodiments in which the instillation event of FIG. 7 corresponds to the instillation of fluid during the continued NPWT treatment of step 512 described with reference to the method 500 of FIG. 5, the initial wound site 114 volume estimate obtained at step 702 may be equal to the wound site 114 volume estimated at step 508 of the method 500 of FIG. 5. In embodiments in which the method 700 of FIG. 7 is performed following a previous iteration of the method 700 of FIG. 7, the wound site 114 volume estimate obtained at step 702 may correspond to the wound site 114 volume estimated at step 720 of the previous iteration of the method 700. In yet other embodiments, the wound site 114 volume estimate obtained at step 702 may be obtained according to any other number of other methods (such as, e.g. a volume estimated at step 810 of the method 800 of FIG. 8).

At step 704, the pneumatic pump 120 is operated to attain a predetermined negative pressure at any one or more of the tubing 110, the removed fluid canister 106, the therapy device 102, at the wound site 114, the pump 120, etc., following which, at step 706 instillation fluid 105 is instilled to the wound site 114. As shown in FIG. 7, as fluid is instilled to the wound site 114, according to some embodiments, pressure at any one or more of the tubing 110, the removed fluid canister 106, the therapy device 102, at the wound site 114, the pump 120, etc. may optionally be monitored in real-time at step 708. In such embodiments, this measured real-time pressure may be compared against a model pressure decay curve (such as described with reference to step 502 in the method 500 of FIG. 5 above) representative of a volume corresponding to the estimated wound site 114 volume obtained at step 702 and the conditions under which instillation fluid 105 is being instilled to the wound site at step 706. As shown in FIG. 7, in the event that the measured real-time pressure decay does not correspond to the expected pressure decay of the model pressure decay curve, at step 710, the controller 118 may generate an alert to the user. In the event that the real-time pressure decay is changing at a rate that is greater than the expected rate, at step 712 the controller 118 may optionally also stop the instillation of instillation fluid 105 to the wound site 114, so as to prevent an overfill of fluid.

As will be understood, the measured real-time pressure decay may vary from the expected pressure decay predicted by the model data for any number of reasons. For example, in embodiments in which the wound site 114 has decreased in volume since the last time that the volume of the wound site 114 had been estimated, it is anticipated that pressure decay observed as a result of the now-smaller dimensioned wound site 114 will vary from the expected pressure decay predicted by the model data. Accordingly, in some embodiments, the controller 118 may be configured to generate an alarm at step 710 and/or stop the instillation of instillation fluid 105 at step 712 only in the event that the difference between the measured pressure decay and the expected pressure decay exceeds a predetermined threshold. According to some embodiments, this threshold may correspond to a difference that is greater than approximately ±15 percent, and more specifically greater than approximately ±10 percent, and even more specifically greater than approximately ±5 percent.

If no difference between the real-time and expected pressure measurement is detected at step 708 (or if the difference does not exceed the predetermined threshold), a determination is made at step 714 as to whether a predetermined target pressure has been attained at any one or more of the tubing 110, the removed fluid canister 106, the therapy device 102, at the wound site 114, the pump 120, etc. If the pressure measured has been determined to be substantially equal to the predetermined target pressure, instillation of the instillation fluid 1045 is stopped at step 716. According to various embodiments, the predetermined target pressure at step 714 may be between approximately minus 15 mmHg and approximately 15 mmHg, more specifically between approximately minus 5 mmHg and 5 mmHg, and even more specifically approximately 0 mmHg.

According to some embodiments, if the target pressure has not yet been attained at step 714, step 706 of instilling fluid to the wound site 114 (and optionally step 708 of comparing monitored pressure to expected pressure based on model data) may be repeated until it is determined at step 714 that the target pressure has been attained.

However, as shown in FIG. 7, according to some embodiments, the method 700 may optionally include step 718, which may provide an additional layer of safeguard against overfill for the NPWT system 100 in the event that the comparison of measured wound site 114 pressure to the target pressure is insufficient to detect a potential overfill situation. In such embodiments, at step 718 a total volume of instillation fluid 105 instilled to the wound site 114 since the initiation of step 706 may be compared against the wound site 114 volume estimate obtained at step 702, with the instillation of instillation fluid 105 being stopped at step 716 if the volume of instilled fluid is determined to be substantially the same as the estimated wound site 114 volume. As will be understood, by preventing the instillation of a volume of a quantity of instillation fluid 105 that exceeds the estimated volume of the wound site 114, step 718 of the method 700 of FIG. 7 provides an additional level of protection against overfill for the NPWT system 100. Alternatively, if the volume of instilled instillation fluid 105 is less than the estimated wound site 114 volume, the method 700 may continue to instill fluid to the wound site 114 at step 706.

According to some embodiments, at step 720, a current volume of the wound site 114 may optionally be estimated based on the most recent instillation of fluid during step 706, with this most recent estimated wound site 114 volume being stored at step 722 for any number of future uses (e.g., for future instillations of fluid according to the method 700 of FIG. 7, to monitor healing of the wound site 114 according to the method 600 of FIG. 6, etc.). In situations in which the instillation of fluid was stopped at step 716 in response to the target pressure being determined to have been attained at step 714, the wound site 114 volume may be estimated in a manner similar to that described with reference to step 508 of the method 500 of FIG. 5, in which the pressure decay observed at any one or more of the tubing 110, the removed fluid canister 106 the therapy device 102, at the wound site 114, the pump 120, etc. during the instillation of fluid is compared to model pressure decay data to identify a corresponding volume of the wound site 114. If instillation of instillation fluid 105 was stopped at step 716 in response to the volume of instilled fluid being determined to be substantially equal to or greater than the estimated wound site 114 volume at step 718, according to some embodiments, the wound site 114 volume estimated at step 720 may correspond to the prior wound site 114 volume estimate.

As noted above, according to some embodiments, it may be desirable to verify the wound site 114 volume estimated during instillation of fluid to the wound site 114 (such as, e.g., described with reference to the method 500 of FIG. 5 and/or the method 700 of FIG. 7) against wound site 114 volume estimates obtained according to any other number of different methods. Referring to FIG. 8, an exemplary embodiment of one such method 800 of verifying a wound site 114 volume estimate obtained during fluid instillation against a wound site 114 volume estimated according to another method, or vice versa, is illustrated. More specifically, in the method 800 illustrated by the flowchart of FIG. 8, a wound site 114 volume estimate based on a dynamic pressure response observed during a purging of various portions of the negative pressure circuit 200 of a NPWT system 100 according to, e.g. the embodiment described with reference to FIG. 4, is compared against a wound site 114 volume estimate based on fluid instillation to provide the NPWT system 100 with a higher confidence wound site 114 volume estimate.

Figure 8:
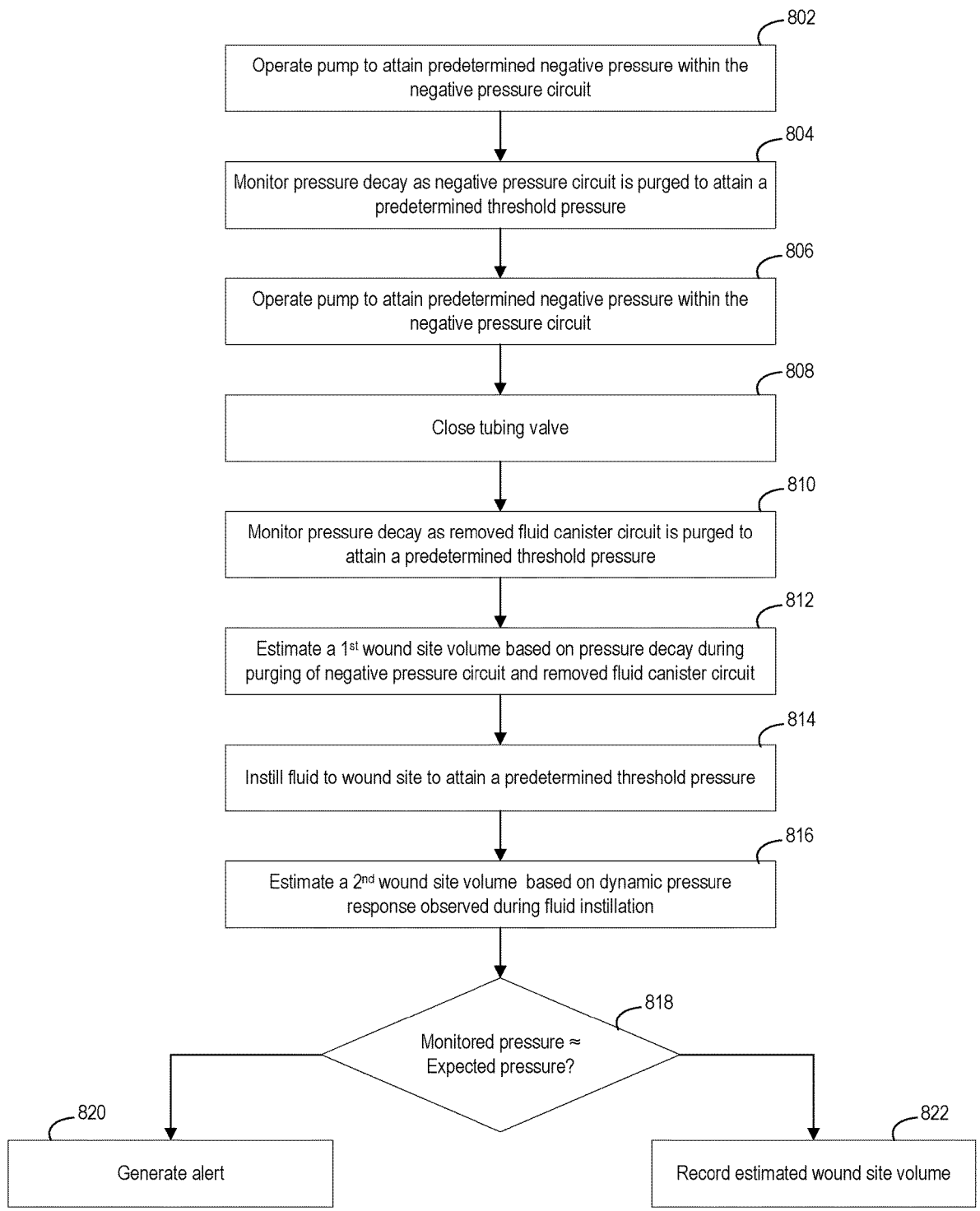
FIG. 8 is a flowchart of a method of using a negative pressure wound therapy system, according to an exemplary embodiment.

As shown in FIG. 8, according to one embodiment of method 800, the pneumatic pump 120 is operated at step 802 to attain a desired negative pressure within the negative pressure circuit 200. As will be understood, in embodiments in which tubing valve 111' is in a closed configuration, step 802 may additionally include the step of opening the tubing valve 111'. Once the desired negative pressure has been attained in the negative pressure circuit 200, the negative pressure circuit 200 is purged by allowing air from the ambient environment to flow into the negative pressure circuit 200 (e.g., via calibrated leak system 113) until a predetermined threshold pressure is attained within the negative pressure circuit 200. As the negative pressure circuit 200 is purged during step 804, pressure decay within the negative pressure circuit 200 is monitored (using, e.g. pressure sensor(s) 115).

Once the predetermined threshold pressure has been attained within the negative pressure circuit 200, the pneumatic pump 120 is once again operated at step 806 to evacuate air from the negative pressure circuit 200 to attain a desired negative pressure with the negative pressure circuit 200. Once this desired negative pressure has been attained, the tubing valve 111' is closed at step 808, thereby fluidly isolating the removed fluid canister circuit from the wound site circuit.

At step 810, the removed fluid canister circuit is purged by allowing air from the ambient environment to flow into the removed fluid canister circuit (e.g., via calibrated leak system 113) until a predetermined threshold pressure is attained within the removed fluid canister circuit. As the removed fluid canister circuit is purged during step 810, pressure decay within the removed fluid canister circuit is monitored (using, e.g. pressure sensor 115). At step 812 a first volume of the wound site 114 is estimated using the pressure decay observed within the negative pressure circuit 200 and the removed fluid canister circuit during steps 804 and 810 respectively. More specifically, the volume of the wound site 114 is calculated by comparing the observed pressure decays from steps 804 and 810 to model pressure decay data to identify corresponding volumes representative of the volumes of the negative pressure circuit 200 and removed fluid canister circuit, from which the wound site 114 may subsequently be estimated. Non-limiting examples of embodiments of additional methods of and/or systems via which wound site 114 volume at may be calculated using observed pressure decay during purging of some or all of the negative pressure circuit 200 as described with reference to steps 802-812 of the method 800 of FIG. 8 are outlined in related, co-pending U.S. Provisional Application 62/714,229, filed Aug. 3, 2018 and titled WOUND THERAPY SYSTEM WITH WOUND VOLUME ESTIMATION, the entire disclosure of which is incorporated by reference herein.

At step 814 instillation fluid 105 is instilled to the wound site 114 until a predetermined pressure has been attained at any one or more of the tubing 110, the removed fluid canister 106, the therapy device 102, at the wound site 114, the pump 120, etc., in a manner similar to that discussed with reference to step 506 of the method 500 of FIG. 5. A second wound site 114 volume is estimated at step 816 based on pressure decay observed at any one or more of the tubing 110, the removed fluid canister 106, the therapy device 102, at the wound site 114, the pump 120, etc. during the instillation of fluid to the wound site 114 at step 814, and in a manner similar to that described with reference to step 508 of the method 500 of FIG. 5. As will be understood, according to some embodiments, steps 814 and 816 may optionally precede, or alternatively be performed simultaneously with, steps 810 and 812.

The first wound site 114 volume estimated at step 812 is compared at step 818 to the second wound site 114 volume estimated at step 816. If the first volume and second volume are determined to not be substantially similar to one another at step 818, an alert may be generated at step 820. If the first volume and second volume are determined to be substantially similar to one another at step 818, one, both, or an averaged value of the first wound site 114 volume estimate and second wound site 114 volume estimate are stored at step 822. As will be understood, any degree of similarity may be used to determine whether the first volume and second volume are substantially similar to one another at step 818. According to some embodiments, the first volume and second volume may be determined to be substantially similar to one another at step 818 if the first volume and second volume differ from one another by approximately no more than 15 percent, more specifically by approximately no more than 10 percent, and even more specifically by approximately no more than 5 percent.

As will be understood, the method 800 of FIG. 8 may be performed any number of times, and at any point during the NPWT treatment provided using the NPWT system 100. For example, according to some embodiments, the method 800 is performed upon an initial use of the NPWT system 100, following which the NPWT system 100 may be operated according to any of the methods disclosed herein, or any other number of different NPWT treatment, or other treatment, protocols. In embodiments in which the method 800 of FIG. 8 is followed by the method 700 of FIG. 7, the wound site 114 volume estimate obtained at step 702 during an initial iteration of method 700 may correspond to the wound site 114 volume estimate stored at step 820 of method 800. In subsequent iterations of method 700, the wound site 114 volume estimate obtained at step 702 may correspond to the wound site 114 volume stored at step 722 during the immediately preceding iteration of method 700.

In other embodiments, some or all of the method 800 of FIG. 8 may be repeated any number of desired times. For example, in some embodiments, the cross-check between wound site 114 volume estimated based on purging the events of step 804 and 810 and wound site 114 volume estimated based on fluid instillation of step 814 may be desired with each iteration of the method 800, in which embodiments the method 800 of FIG. 8 may be repeated in its entirety with each iteration. In other embodiments, it may be desired to alternate estimation of wound site 114 volume based on the purging events of step 804 and 810 with the estimation of wound site 114 volume based on the fluid instillation at step 814. Additionally, according to various embodiments, (including those embodiments of FIG. 8 discussed above) some or all of the iterations of the method 800 of FIG. 8 may optionally incorporate some or all of the steps 708, 710, 712, 714, 716, 718, and 720 of the method 700 of FIG. 700 between steps 815 and 816. According to various embodiments, the method 600 of monitoring wound site 114 healing of FIG. 6 may also be incorporated into any of the methods disclosed herein.

In general, the volume of the wound site 114 is defined by the entirety of the interior extending between the wound site 114 and the drape layer 117 attached to the skin 116 about the wound site 114. At various points during treatment using the NPWT system 100, located within and defining the volume of the wound site may be any one of, and any combination of: the wound dressing 112, fluid 121, and/or dead space 119. As will be understood, unless the wound dressing 112 is replaced during treatment, the volume of the wound site 114 volume occupied by the wound dressing 112 will generally remain unchanged over the course of treatment, whereas the portion of the wound site 114 volume occupied by the fluid 121 and/or dead space 119 may change with time.

As will be understood, according to various embodiments, the controller 118 may be programmed to allow the NPWT system 100 to determine volume relative to the wound site 114 using any or all of the methods described herein.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied, and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general-purpose computer, special purpose computer, or special purpose processing machines to perform a certain function or group of functions.

Although the figures show a specific order of method steps, the order of the steps may differ from what is depicted. Also, two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps and decision steps.

We claim:

1. A method comrprising:
fluidly connecting a fluid tube to a fluid canister, a pump of a therapy device and a wound dressing applied to a wound site;
operating the pump until a predetermined first negative pressure is detected;
instilling a first quantity of fluid to the wound site until a first predetermined target pressure is detected;
monitoring pressure during instillation of the first quantity of fluid to the wound site; and
determining a volume of the first quantity of fluid instilled to the wound site by comparing pressure measurements obtained from the monitored pressure during the instillation of the first quantity of fluid to the wound site to model pressure decay data.

2. The method of claim 1, wherein the model pressure decay data is representative of pressure decay within a container having a known volume as a predetermined quantity of fluid is instilled to the container.

3. The method of claim 1, further comprising operating the pump until a predetermined second negative pressure is detected.

4. The method of claim 3, further comprising instilling a second quantity of fluid to the wound site until a second predetermined target pressure is detected.

5. The method of claim further comprising determining a volume of the second quantity of fluid instilled to the wound site using pressure measurements obtained from monitoring pressure during the instillation of the second quantity of fluid to the wound site.

6. A method of preventing overfill of fluid to a wound site, the method comprising:
fluidly connecting a fluid tube to a fluid canister, a pump of a therapy device and a wound dressing applied to a wound site;
operating the pump to attain a predetermined first negative pressure:
instilling a fluid to the wound site;
monitoring pressure during instillation of the fluid to the wound site;
stopping the instillation of fluid to the wound site in response to a first predetermined target pressure being detected; and
determining a volume of the fluid instilled to the wound site by comparing pressure measurements obtained during instillation of the fluid to the wound site to model pressure decay data.

7. The method of claim 6, wherein a volume of the wound site is estimated prior to the instillation of fluid to the wound site.

8. The method of claim 7, further comprising obtaining the model. pressure decay data representative of pressure decay within a container having a volume equal to the estimated volume of the wound site as varying quantities of fluid are instilled into the container.

9. The method of claim 6, wherein monitoring pressure includes obtaining measurements of pressure at the wound site.

10. The method of claim 9, wherein the obtained pressure measurements are compared to the model pressure decay data in real-time and an alarm is generated if the measure pressure does not correspond to the model pressure decay data.

11. The method of claim 6, further comprising:
estimating a volume of the wound site prior to the instillation of the fluid to the wound site; and
comparing the estimated volume of the wound site to the determined volume of the fluid instilled to the wound site;
wherein an alarm is generated if the estimated volume of the wound site is not substantially the same as the determined volume of the fluid instilled to the wound site.

* * * * *

UNITED STATES PATENT AND TRADEMARK OFFICE
CERTIFICATE OF CORRECTION

PATENT NO. : 11,471,573 B2
APPLICATION NO. : 16/366308
DATED : October 18, 2022
INVENTOR(S) : Justin Rice Page 1 of 1

It is certified that error appears in the above-identified patent and that said Letters Patent is hereby corrected as shown below:

In the Claims

Column 18
Line 7, In Claim 5, delete "claim" and insert -- claim 4, --, therefor.
Line 33, In Claim 8, after "model", delete ".".

Signed and Sealed this
Ninth Day of April, 2024

Katherine Kelly Vidal
*Director of the United States Patent and Trademark Office*